US012729404B2

(12) United States Patent
Chung et al.

(10) Patent No.: US 12,729,404 B2
(45) Date of Patent: Sep. 8, 2026

(54) METHOD AND KIT FOR TESTING DRUG HYPERSENSITIVITY REACTIONS CAUSED BY SULFONAMIDE DERIVATIVE-BASED ANTIEPILEPTIC DRUG AND USE OF THE KIT

(71) Applicant: CHANG GUNG MEMORIAL HOSPITAL, LINKOU, Taoyuan (TW)

(72) Inventors: Wen-Hung Chung, Taoyuan (TW); Shuen-Iu Hung, Taoyuan (TW); Chuang-Wei Wang, Taoyuan (TW)

(73) Assignee: Chang Gung Memorial Hospital, Linkou, Taoyuan (TW)

( * ) Notice: Subject to any disclaimer, the term of this patent is extended or adjusted under 35 U.S.C. 154(b) by 658 days.

(21) Appl. No.: 18/021,427

(22) PCT Filed: Aug. 16, 2021

(86) PCT No.: PCT/CN2021/112752

§ 371 (c)(1),
(2) Date: Feb. 15, 2023

(87) PCT Pub. No.: WO2022/037524

PCT Pub. Date: Feb. 24, 2022

(65) Prior Publication Data

US 2024/0035089 A1 Feb. 1, 2024

(30) Foreign Application Priority Data

Aug. 18, 2020 (AU) ................................ 2020902931

(51) Int. Cl.

| | |
|---|---|
| ***C12Q 1/68*** | (2018.01) |
| ***C07H 21/04*** | (2006.01) |
| ***C12Q 1/6827*** | (2018.01) |
| ***C12Q 1/6881*** | (2018.01) |

(52) U.S. Cl.

CPC ......... *C12Q 1/6881* (2013.01); *C12Q 1/6827* (2013.01); *C12Q 2600/106* (2013.01); *C12Q 2600/156* (2013.01)

(58) Field of Classification Search

None

See application file for complete search history.

(56) References Cited

U.S. PATENT DOCUMENTS

| | | | |
|---|---|---|---|
| 2015/0218634 A1 | 8/2015 | Zhang et al. | |
| 2019/0226023 A1 | 7/2019 | Chung et al. | |

FOREIGN PATENT DOCUMENTS

| | | | | |
|---|---|---|---|---|
| CN | 102925567 A | 2/2013 | | |
| CN | 104818316 A | 8/2015 | | |
| CN | 104818316 B | 9/2018 | | |
| WO | 2018076228 A1 | 5/2018 | | |
| WO | WO-2021030925 A1 * | 2/2021 | ......... | G01N 33/6893 |

OTHER PUBLICATIONS

Huyen et al. (J. Med Sci. vol. 8(B) pp. 395-400, Jun. 10, 2020) (Year: 2020).*

Request for the Submission of an Opinion dated Aug. 1, 2025 in Korean application No. KR 20237008283.

Office action dated Jul. 18, 2023 in Taiwanese application No. TW 110130066.

Ji-Yeon Lee et al., "A Case of Zonisamide-Induced Stevens-Johnson Syndrome," The Korean Association of Internal Medicine, Dec. 31, 2015, vol. 89, No. 3.

Fa-Yun Hu et al., "Phenytoin-Induced Stevens-Johnson Syndrome with Negative HLA-B1502 Allele in Mainland China: Two Cases," Seizure, Dec. 31, 2011, pp. 431-432, vol. 20, No. 5.

International Search Report and Written Opinion for PCT/CN2021/112752, mailed Oct. 29, 2021.

Office Action in Taiwan Application No. 110130066, dated Nov. 22, 2022.

Laura Maurer BS et al., "A Delayed Presentation of Acute Generalized Exanthematous Pustulosis (AGEP)," Int J Clin Med Allergy, May 2015, pp. 11-13, vol. 03(1).

Office action dated Dec. 31, 2025 in Chinese application No. 202180055691.3.

* cited by examiner

*Primary Examiner* — Jeanine A Goldberg

(74) *Attorney, Agent, or Firm* — Pilloff Passino & Cosenza LLP; Rachel K. Pilloff; Sean A. Passino

(57) ABSTRACT

The present invention provides a method for assessing the risk of drug hypersensitivity reaction caused by an antiepileptic drug with a sulfonamide derivative in a subject in need of such an assessment, comprising the step of detecting the presence of HLA-B alleles in the sample obtained from the subject, wherein the presence of the allele indicates that the subject has an increased risk of developing drug hypersensitivity reaction caused by the antiepileptic drug with the sulfonamide derivative. The present invention also provides a method for treating or reducing the incidence of such drug hypersensitivity reaction. Also provided are a test kit for assessing the risk of a patient developing drug hypersensitivity reaction caused by an antiepileptic drug with a sulfonamide derivative, comprising a reagent for determining specific HLA alleles, and use of the test kit in assessing the risk of a patient developing drug hypersensitivity reaction caused by an antiepileptic drug with a sulfonamide derivative.

10 Claims, No Drawings

METHOD AND KIT FOR TESTING DRUG HYPERSENSITIVITY REACTIONS CAUSED BY SULFONAMIDE DERIVATIVE-BASED ANTIEPILEPTIC DRUG AND USE OF THE KIT

CROSS-REFERENCE TO RELATED APPLICATIONS

Technical Field

This application claims priority to the benefit of Australian Provisional Application No. 2020902931 filed on 18 Aug. 2020, the entire content of which is incorporated herein by reference.

Background Technique

Drug Hypersensitivity Reaction is a drug-induced, potentially fatal immune disease, including milder skin rashes (maculopapular eruptions, MPE), erythema multiforme majus (EMM), and fixed drug eruption (FDE), to severe and potentially fatal severe cutaneous adverse reactions (SCAR), including drug reaction with eosinophilia and systemic symptoms (DRESS), Stevens-Johnson syndrome (SJS), and toxic epidermal necrolysis (TEN).

Drug allergy is often related to immune response, but the immune mechanism is very complex. For example, there are more than 300 genotypes for HLA-A alleles and more than 600 genotypes for HLA-B. Therefore, it is difficult to identify the immune mechanisms that cause adverse drug reactions.

Sulfonamide drugs refer to drugs with a sulfonamide group (chemical formula $SO_2NH_2$), such as the anti-epileptic zonisamide. There are many cases of drug hypersensitivity reaction in clinical setting caused by antiepileptic drugs with sulfonamide derivatives.

Therefore, there is a need for a method to assess the risk of developing a drug hypersensitivity reaction induced by an antiepileptic drug with a sulfonamide derivative in a subject, and methods of treating or reducing the incidence of drug hypersensitivity reaction induced by such drug. The present invention addresses this and other needs.

SUMMARY OF THE INVENTION

According to an object of the present invention, a method for assessing the risk of developing drug hypersensitivity reaction caused by an antiepileptic drug with a sulfonamide derivative in a subject is disclosed, comprising the following steps:

(a) detecting the presence of HLA-B*13:01, HLA-B*51:01 or HLA-B*51:02 allele in the subject's sample, and
(b) the presence of the HLA-B*13:01, HLA-B*51:01, or HLA-B*51:02 allele indicates the subject has a higher risk of developing drug hypersensitivity reaction caused by an antiepileptic drug with a sulfonamide derivative.

In one embodiment, the presence of HLA-B*13:01, HLA-B*51:01 or HLA-B*51:02 allele is determined by an oligonucleotide that specifically hybridizes to the allele.

In one embodiment, the antiepileptic drug with a sulfonamide derivative is zonisamide.

In one embodiment, the detection of HLA-B*13:01 and HLA-B*51:01 in a sample of the subject is included.

In one embodiment, the detection of HLA-B*13:01 and HLA-B*51:02 in a sample of the subject is included.

In one embodiment, the drug hypersensitivity reaction comprises at least one of the following adverse reactions: maculopapular eruption (MPE), fixed drug eruption (FDE), Stevens-Johnson Syndrome (SJS), toxic epidermal necrolysis (TEN) or drug rash with eosinophilia and systemic symptoms (DRESS).

According to another object of the present invention, a test kit for assessing the risk of a patient developing a drug hypersensitivity reaction caused by an antiepileptic drug with a sulfonamide derivative is disclosed, the test kit comprising a reagent for detecting HLA-B*13:01, HLA-B*51:01 or HLA-B*51:02 allele in a patient's sample.

In one embodiment, the test kit comprises an oligonucleotide that specifically hybridizes to the nucleic acids of HLA-B*13:01, HLA-B*51:01 or HLA-B*51:02 allele.

According to another object of the present invention, a kit for detecting HLA-B*13:01, HLA-B*51:01 or HLA-B*51:02 allele is disclosed, for use in the development of assessing the risk of drug hypersensitivity reaction induced by an antiepileptic drug with a sulfonamide derivative.

In one embodiment, the kit comprises an oligonucleotide that specifically hybridizes to the nucleic acids of HLA-B*13:01, HLA-B*51:01 or B*51:02 allele.

According to another object of the present invention, a method for evaluating the risk of developing a drug hypersensitivity reaction caused by an antiepileptic drug with a sulfonamide derivative and treating the drug hypersensitivity reaction caused by the antiepileptic drug with a sulfonamide derivative is disclosed, comprising the following steps:

(a) detecting the presence of HLA-B*13:01, HLA-B*51:01 or HLA-B*51:02 allele in the sample of a subject;
(b) the presence of HLA-B*13:01, HLA-B*51:01 or HLA-B*51:02 allele indicates an increased risk of developing drug hypersensitivity reaction in the subject; and
(c) administering a drug to treat the drug hypersensitivity reaction.

According to another object of the present invention, a method for evaluating the risk of developing a drug hypersensitivity reaction induced by an antiepileptic drug with a sulfonamide derivative and treating the drug hypersensitivity reaction caused by the antiepileptic drug with a sulfonamide derivative is disclosed, comprising the following steps:

(a) detecting the presence of HLA-B*13:01, HLA-B*51:01 or HLA-B*51:02 allele in the sample of a subject;
(b) the presence of HLA-B*13:01, HLA-B*51:01 or HLA-B*51:02 allele indicates an increased risk of developing drug hypersensitivity reaction in the subject; and
(c) administering an antiepileptic drug without a sulfonamide derivative.

According to another object of the present invention, a method for assessing the risk of developing severe cutaneous adverse reaction in a subject induced by an antiepileptic drug with a sulfonamide derivative, comprising the following steps:

(a) detecting the presence of HLA-B*51:01 or HLA-B*51:02 allele in the sample of a subject, and
(b) the presence of HLA-B*51:01 or HLA-B*51:02 allele indicates an increased risk of developing severe cutaneous adverse reaction caused by an antiepileptic drug with a sulfonamide derivative.

In one embodiment, the method further comprises detecting HLA-B*13:01 allele.

In one embodiment, the presence of HLA-B*13:01, HLA-B*51:01 or HLA-B*51:02 allele is determined by an oligonucleotide that specifically hybridizes to the allele.

In one embodiment, the antiepileptic drug with a sulfonamide derivative is Zonisamide.

In one embodiment, the sample is DNA, RNA, protein, cells, serum, peripheral blood, saliva, urine, hair or skin.

In one embodiment, the severe cutaneous adverse reaction comprises at least one of the following adverse reactions: Stevens Johnson Syndrome (SJS), toxic epidermal necrolysis (TEN) or drug rash with eosinophilia and systemic symptoms (DRESS).

According to another object of the present invention, a test kit for assessing the risk of severe cutaneous drug reaction caused by an anti-epileptic with a sulfonamide derivatives in a patient is disclosed, the test kit includes a reagent for detecting HLA-B*51:01 or HLA-B*51:02 allele in the sample of the patient.

In one embodiment, the test kit further comprises detecting HLA-B*13:01 allele.

In one embodiment, the test kit comprises an oligonucleotide that specifically hybridizes to the nucleic acids of HLA-B*13:01, HLA-B*51:01 or HLA-B*51:02 allele.

According to another object of the present invention, a test kit for detecting HLA-B*51:01 or B*51:02 allele, for use in the development of assessing the risk of developing severe cutaneous adverse reactions caused by an antiepileptic drug with sulfonamide derivative is disclosed.

In one embodiment, the use further comprises determining the HLA-B*13:01 allele.

In one embodiment, the test kit comprises an oligonucleotide that hybridizes specifically to nucleic acids of the HLA-B*13:01, HLA-B*51:01 or HLA-B*51:02 alleles.

According to another object of the present invention, a method for evaluating the risk of developing severe cutaneous adverse reaction caused by an anti-epileptic drug with a sulfonamide derivative and treating the severe cutaneous adverse reaction caused by an anti-epileptic drug with a sulfonamide derivatives is disclosed, comprising the following steps:

(a) detecting the presence of HLA-B*51:01 or HLA-B*51:02 allele in a subject's sample;
(b) the presence of HLA-B*51:01 or HLA-B*51:02 allele indicates an increased risk of developing severe cutaneous adverse reaction in the subject; and
(c) administering a drug to treat said severe cutaneous adverse reaction.

According to another object of the present invention, a method for assessing the risk of developing severe cutaneous adverse reaction caused by an antiepileptic drug with a sulfonamide derivative and treating the severe cutaneous adverse reaction caused by an antiepileptic drug with sulfonamide derivative is disclosed, comprising the following steps:

(a) detecting the presence of HLA-B*51:01 or HLA-B*51:02 allele in a subject's sample;
(b) the presence of HLA-B*51:01 or HLA-B*51:02 allele indicates an increased risk of developing severe cutaneous adverse reaction in the subject; and
(c) administering an antiepileptic drug without a sulfonamide derivative.

In one embodiment, the use further comprises detecting the presence of the HLA-B*13:01 allele in the sample of the subject.

As used herein, the term "invention" as used in this patent is intended to refer broadly to all of the subject matter of this patent and the following patent claims. Statements containing these terms should be understood not to limit the subject matter described herein or to limit the meaning or scope of the following patent claims. Embodiments of the invention covered by this patent are defined by the following claims rather than this summary. This summary is a high-level overview of various aspects of the invention and introduces some concepts that are further described in the following description section. This summary is not intended to identify key features or essential features of the claimed subject matter, nor is it intended to be used alone to determine the scope of the claimed subject matter. The subject matter should be understood by reference to the appropriate portions of the entire specification, any or all drawings, and the claims.

The present invention will become clearer when reading the following embodiments.

Implementation

As used herein, the article "a" refers to one or more than one (i.e., at least one) grammatical object.

The terms "subject" and "patient" are used interchangeably to refer to vertebrates in which drug hypersensitivity reactions (DHRs) may occur. Subjects may include warm-blooded animals, such as mammals, such as primates, preferably humans.

As used herein, the term "treatment" refers to both therapeutic treatment and prophylactic or preventive measures; persons in need of treatment may include those who have developed DHR, or subjects prone to DHR or in need of DHR prevention.

In an embodiment of the present invention, the drug hypersensitivity reaction (DHR) is a delayed type hypersensitivity. The manifestations of DHR include mild maculopapular exanthema (MPE), fixed drug eruptions (FDEs), even life-threatening severe cutaneous adverse reactions (SCAR). SCAR includes drug rash with eosinophilia and systemic symptoms (DRESS), Stevenson-Johnson Syndrome (SJS) and toxic epidermal necrolysis (TEN).

The present invention further provides a method for assessing the risk of developing a drug hypersensitivity reaction and treating the drug hypersensitivity reaction induced by an antiepileptic drug with a sulfonamide derivative, such as zonisamide, comprising the following steps:

(a) detecting the presence of HLA-B*13:01, HLA-B*51:01 or HLA-B*51:02 allele in the sample of a subject;
(b) the presence of HLA-B*13:01, HLA-B*51:01 or B*51:02 allele indicates an increased risk of developing drug hypersensitivity reaction in the subject; and
(c) administering a drug to treat said drug hypersensitivity reaction.

The present invention further provides a method for assessing the risk of developing a drug hypersensitivity reaction and treating the drug hypersensitivity reaction induced by an antiepileptic drug with a sulfonamide derivative, such as zonisamide, comprising the following steps:

(a) detecting the presence of HLA-B*13:01, HLA-B*51:01 or HLA-B*51:02 allele in the sample of a subject;
(b) the presence of HLA-B*13:01, HLA-B*51:01 or HLA-B*51:02 allele indicates an increased risk of developing drug hypersensitivity reaction in the subject; and
(c) administering an antiepileptic drug without a sulfonamide derivative.

In an exemplary embodiment, the method of reducing the incidence of drug hypersensitivity reactions induced by an antiepileptic drug with a sulfonamide derivative is achieved by administering an antiepileptic drug without a sulfonamide derivative. In another exemplary embodiment, the method of treating a drug hypersensitivity reaction induced by an antiepileptic drug with a sulfonamide derivative is by administering a drug to treat the drug hypersensitivity reaction, including, but not limited to, fluids, corticosteroids, intravenous immunoglobulin, cyclosporine, anti-TNF-α agents, or plasmapheresis.

In some embodiments, the risk allele (HLA-B*13:01, HLA-B*51:01 or HLA-B*51:02) can be detected by any method known in the art, including but not limited to HLA A typing, serological or microcytotoxic method, or an equivalent genetic marker to detect the allele. The "equivalent genetic marker" of the risk allele refers to a genetic marker linked to the target allele (which shows linkage disequilibrium with the target allele) and can be, for example, a SNP (single nucleotide polymorphism), microsatellite markers, or other types of genetic polymorphisms. In one embodiment, the genomic DNA is hybridized with a probe specific for the variant of interest. A probe can be labeled for direct detection, or contacted with a second detectable molecule that specifically binds to the probe. Alternatively, the cDNA, RNA or protein product of the variant can be detected.

The risk HLA alleles can be directly detected from the genomic DNA prepared from the sample of a subject, including but not limited to blood, saliva, urine or hair, to detect the regions/nucleotides within the allele.

Example

Table 1. Association of HLA-B alleles with zonisamide-induced drug hypersensitivity reaction (DHR) in Han ethics group.

TABLE 1

Association of HLA-B alleles with zonisamide-induced DHR

| HLA Allele | DHR N (%) | General Population N (%) | Odds Ratio (OR) (95% CI) | P value |
|---|---|---|---|---|
| HLA-B*13:01 | 3/3 (100%) | 234/2038 (11.48% ) | 53.87 (2.8 to 1046.1) | 0.0015 |

Three patients with zonisamide-induced drug hypersensitivity reaction (DHR) were recruited for this study and their HLA typing was assessed by sequencing-based typing (SBT) and compared with 2038 healthy subjects. The results show that all 3 patients with drug hypersensitivity reaction carried HLA-B*1301 allele (100%). In contrast, 234 of 2038 healthy subjects carried the HLA-B*1301 allele (11.48%). Statistical analysis further shows that the presence of HLA-B*1301 allele was significantly associated with zonisamide-induced drug hypersensitivity reactions (DHR vs. control: $P=1.5\times10^{-3}$; OR=53.87 (2.8-1046.1); sensitive: 100.00%; Specificity: 88.52%) (see Table 1). Based on the above results, the HLA-B*1301 allele can be used to assess the risk of developing drug hypersensitivity reaction induced by zonisamide.

TABLE 2

Association of HLA-B alleles with zonisamide-induced severe cutaneous adverse reactions (SCARs).

| Group | Cases N (%) | General Population N (%) | OR (95% CI) | P value |
|---|---|---|---|---|
| HLA-B*13:01 SCAR | 5/7 (71.4%) | 234/2038 (11.5%) | 19.3 (3.7-99.9) | $3.6 \times 10^{-4}$ |
| HLA-B*51:01 or B*51:02 SCAR | 4/7 (57.1%) | 281/2038 (13.8%) | 8.3 (1.9-37.4) | 0.009 |
| The combination of HLA-B*13:01 and (HLA-B*51:01 or HLA-B*51:02) SCAR | 7/7 (100%) | 499/2038 (24.5%) | 46.2 (2.6-810.9) | $5.5 \times 10^{-5}$ |

Table 2 compares the differences of HLA-B allele in 7 patients with zonisamide-induced SCAR (cases) and 2038 healthy controls without a past history of drug hypersensitivity reaction (general population). The results show that HLA-B*13:01 was significantly associated with zonisamide-SCAR. (the presence of the allele is in 71.4% SCAR cases; OR=19.3; 95% CI=3.7-99.9; $p=3.6\times10^{-4}$) (Table 2), and HLA-B*51:01 or HLA-B*51:02 are also significantly associated with zonisamide-SCAR (the presence of the allele is in 57.1% of SCAR cases; OR=8.3; 95% CI=1.9-37.4; p=0.009).

The above-mentioned embodiments merely illustrate the principle and effect of the present invention, but are not intended to limit the present invention. Anyone skilled in the art can modify and change the above embodiments without departing from the spirit and scope of the present invention. Therefore, the scope of protection of the present invention should be based on the claims of the present invention.

The invention claimed is:

1. A method of reducing the incidence of a severe cutaneous adverse reaction (SCAR) induced by zonisamide in a subject in need of an anti-epileptic drug, comprising:

(a) Obtaining a sample from the subject in need of an anti-epileptic drug, (b) Detecting the presence of HLA-B*51:02 allele in the sample from the subject, (c) Identifying the subject as having the SCAR induced by zonisamide or at risk of developing the SCAR induced by zonisamide; and thereafter (d) Administering an antiepileptic drug that is not zonisamide to the subject having HLA-B*51:02 allele.

2. The method of claim 1, wherein the SCAR comprises at least one of the following adverse reactions: Stevenson Johnson Syndrome (SJS), toxic epidermal necrolysis (TEN) or drug rash with eosinophilia and systemic symptoms (DRESS).

3. The method of claim 1, further comprising detecting the presence of HLA-B*13:01 allele.

4. The method of claim 3, wherein the presence of the HLA-B*13:01 allele and HLA-B*51:02 allele is determined by an oligonucleotide that specifically hybridizes to the allele.

5. The method of claim 1, wherein the sample is DNA, RNA, protein, cells, serum, peripheral blood, saliva, urine, hair or skin.

6. A method of reducing the incidence of a severe cutaneous adverse reaction (SCAR) induced by zonisamide in a subject in need of an anti-epileptic, comprising the following steps:

(a) obtaining a sample from the subject, wherein the subject exhibits one or more symptoms of the SCAR induced by zonisamide or is at risk of developing the SCAR induced by zonisamide, (b) detecting the presence of HLA-B*51:02 allele from the sample of the subject;

(c) identifying the subject as having the SCAR induced by zonisamide or at risk of developing the SCAR induced by zonisamide based on the detecting the presence of HLA-B*51:02 allele in step (b); and thereafter (d) administering the antiepileptic drug that is not zonisamide to the subject having the SCAR induced by zonisamide or at risk of developing the SCAR induced by zonisamide.

7. The method of claim 6, wherein the SCAR comprises at least one of the following adverse reactions: Stevenson Johnson Syndrome (SJS), toxic epidermal necrolysis (TEN) or drug rash with eosinophilia and systemic symptoms (DRESS).

8. The method of claim 6, further comprising detecting the presence of HLA-B*13:01 allele.

9. The method of claim 8, wherein the presence of the HLA-B*13:01 allele and HLA-B*51:02 allele is determined by an oligonucleotide that specifically hybridizes to the allele.

10. The method of claim 6, wherein the sample is DNA, RNA, protein, cells, serum, peripheral blood, saliva, urine, hair or skin.

* * * * *